United States Patent [19]
Shimizu

[11] Patent Number: 5,607,590
[45] Date of Patent: Mar. 4, 1997

[54] MATERIAL FOR MEDICAL USE AND PROCESS FOR PREPARING SAME

[76] Inventor: Yasuhiko Shimizu, 39-676, Ogurayama, Kohata, Uji-shi, Kyoto-fu, Japan

[21] Appl. No.: 286,559

[22] Filed: Aug. 5, 1994

Related U.S. Application Data

[63] Continuation-in-part of Ser. No. 178,792, Jan. 7, 1994, abandoned.

[30] Foreign Application Priority Data

Aug. 6, 1993 [JP] Japan .................................. 5-195755
Sep. 1, 1993 [JP] Japan .................................. 5-217628

[51] Int. Cl.$^6$ .................................................. B01D 71/06
[52] U.S. Cl. ........................ 210/490; 210/500.27; 264/41
[58] Field of Search ............................. 210/490, 500.27, 210/500.29; 264/41, 49; 427/2.31, 2.3, 2.24; 623/1

[56] References Cited

U.S. PATENT DOCUMENTS

| | | | |
|---|---|---|---|
| 4,820,302 | 4/1989 | Woodroof | 623/8 |
| 5,131,907 | 7/1992 | Williams et al. | 600/36 |
| 5,219,895 | 6/1993 | Kelman et al. | 522/68 |

FOREIGN PATENT DOCUMENTS

| | | |
|---|---|---|
| 2055099 | 5/1993 | Canada. |
| 0194192 | 9/1986 | European Pat. Off.. |
| WO89/08467 | 3/1989 | WIPO. |

OTHER PUBLICATIONS

S. D. Gorham, *Urological Research*, vol. 15, No. 1, pp. 53–59 (1987).

J. A. M. Ramshaw et al., *Journal of Biomedical Materials Research*, vol. 23, No. 6, pp. 649–660 (1989).

R. N. Meddings et al., *Journal of Pediatric Surgery*, vol. 28, No. 5, pp. 660–663 (1993).

C. G. Gemmell et al., *Urological Research*, vol. 16, No. 5, pp. 381–384 (1988).

R. Scott et al., *British Journal Of Urology*, vol. 68, No. 4, pp. 421–424 (1991).

G. Rachlin et al., *Journal de Parodontologie*, vol. 10, No. 3, pp. 289–293 (1991).

U. R. Shettiger et al., *Artificial Organs*, vol. 6, No. 3, pp. 256–260 (1982).

European Patent Office, European Search Report dated Nov. 23 1994 for European Patent Application No. 94 11 2117.

*Primary Examiner*—Frank Spear
*Attorney, Agent, or Firm*—Finnegan, Henderson, Farabow, Garrett & Dunner, L.L.P.

[57] ABSTRACT

There are disclosed a material for medical use comprising two sheets of collagen membrane adhered to each other with an adhesive and having interposed therebetween a mesh-like intermediary material, wherein the mean pore size of the mesh-like intermediary material is between 100 and 2000 μm; and a process for preparing a material for medical use comprising (a) laminating with an adhesive two sheets of a collagen membrane having a mesh-like intermediary material interposed therebetween; (b) maintaining the resulting laminated material under a reduced pressure so that the two sheets of collagen membrane are adhered to each other through the mesh-like intermediary; and (c) cross-linking the laminated material.

23 Claims, No Drawings

MATERIAL FOR MEDICAL USE AND PROCESS FOR PREPARING SAME

This is a continuation-in-part application of U.S. Ser. No. 08/178,792 of Jan. 7, 1994, now abandoned.

BACKGROUND OF THE INVENTION

The present invention relates to a material for medical use and a process for preparing the same, and more specifically a material for medical use which is applicable to an artificial organ and an artificial viscus, furthermore, which is applicable as a wound covering material, a wound prosthetic material, a wound curing material, a postoperative adhesion-preventing material and the like, and a process for preparing the same.

It has long been known that, when a living tissue has some disorders, is damaged, or has dysfunction, an artificial material is used for replacement, prosthesis, or prevention of adhesion of damaged parts, and it has been conventionally investigated to use a synthetic high molecular material or a material originating from a living body for vessels, air tubes, esophagi, valves, various viscera, and wounds. Such a material is required to satisfy various requirements such as, having an affinity for a living body; having a compatibility with body fluids such as blood, or tissues; having neither toxicity nor antigenicity; and having a mechanical strength as predetermined depending on the implant site.

Generally, a material originating from a living body may possibly cause disorders associated with implantation or immunological responses. However, a collagen, a material originating from a living body, has excellent affinity for a living body and tissue-compatibility, possesses low antigenicity. Collagen also facilitates activity on elongation and proliferation of host cells, as utilized as a medium for cell culture, and has styptic activity. It also has excellent properties as a material for medical use since it is completely absorbed in a living body. However, when only the collagen only is used, it is difficult to form therefrom a material which has a high invading ability into cells and a high proliferating ability for host cells, and also has a considerable mechanical strength. Therefore, collagen has been conventionally used as a composite material with a synthetic high molecular material.

Such a composite material for medical use is produced by forming a covering layer of collagen comprising an alkaline-solubilized collagen or an enzyme-solubilized collagen, having reduced antigenicity, on a surface of the synthetic high molecular material. The synthetic high molecular material may comprise a silicone, a polytetrafluoroethylene, a polyethylene, a polypropylene, a polyethylene terephthalate, a polyurethane, a polyvinyl alcohol and a nylon in the form of film, sheet, woven fabric, non-woven fabric, tube, sponge and the like. The composite may be formed by a coating or a flowing method, and by solidifying the covering layer of collagen by a freeze-drying method and the like. The surface of the synthetic high molecular material is subjected to a hydrophilization treatment by plasma irradiation and the like, so as to improve the affinity for living tissue or the covering layer of collagen.

Another material for medical use has been proposed wherein a material degradable in a living body, having a considerable mechanical strength, which is hydrolyzed or enzymatically decomposed and absorbed in a living body, is combined with collagen.

The material for medical use is produced by solidifying a covering layer comprising an alkaline-solubilized collagen or an enzyme-solubilized collagen, by the above method, on a surface of a material degradable in a living body in the form of film, sheet, woven fabric, or non-woven fabric, comprising a polyglycolic acid, a copolymer of glycolic acid and lactic acid, or a mixture of a polyglycolic acid and a polylactic acid. When the material is implanted in a living body, not only collagen but also the degradable material is hydrolyzed or enzymatically decomposed, and absorbed in the living body, so that it is not necessary to remove the material by conducting another operation again or an endoscopy. The material degradable in a living body is also subjected to a hydrophilization treatment with plasma irradiation as well as the synthetic high molecular material.

However, such a material has a disadvantage in the transfixing property that, when an intermediary material comprising a material degradable in a living body in the form of woven fabric or non-woven fabric, equipped with a covering layer of collagen, is sutured with an organ or a wound, a surgical needle cannot easily pass through a hole in the material. Even if the needle can pass through the hole, force added to the covering layer of collagen may destroy the covering layer of collagen having a small mechanical strength. This material has another disadvantage in that although the affinity for a collagen solution is improved by plasma irradiation on the surface of the intermediary material, the covering layer of collagen may peel from the intermediary material after implantation because of insufficient adhesion between the intermediary material and the covering layer of collagen. In such a case, it is required to conduct another operation to implant the material.

SUMMARY OF THE INVENTION

The present invention was developed in order to solve the foregoing problems. Accordingly an object of the present invention is to provide a material for medical use which is applicable to an artificial organ or an artificial viscus, and further applicable as a wound covering material, a wound prosthetic material, a wound curing material, a post-operative adhesion-preventing material and the like, is excellent in affinity for a living body, tissue compatibility, and mechanical strength, possesses low antigenicity, and is particularly excellent in its transfixing property. It is also an object of the invention to provide a process for preparing the same.

The material for medical use of the present invention comprises two sheets of collagen membrane adhered to each other with an adhesive, and having interposed therebetween a mesh-like intermediary material, wherein the mean pore size of the mesh-like intermediary material is between 100 and 2000 µm. The process for preparing the same comprises laminating with an adhesive two sheets of collagen membrane having a mesh-like intermediary material interposed therebetween, wherein the mean pore size of the mesh-like intermediary material is between 100 and 2000 µm; maintaining the resulting laminated material under a reduced pressure so that the two sheets of collagen membrane are adhered to each other; and cross-linking the laminated material. Furthermore, the process may comprise subjecting the laminated material to a succinylation treatment, depending upon the purpose.

DESCRIPTION OF THE PREFERRED EMBODIMENTS

In the following, the present invention is explained in detail.

As collagen usable as the material for the collagen membrane of the present invention, various collagens can be used. There can be mentioned, for example, a neutral solubilized collagen, an acid-solubilized collagen, an alkali-solubilized collagen, an enzyme-solubilized collagen and the like. Among them, the alkali-solubilized collagen and the enzyme-solubilized collagen which are obtained by treating an insoluble collagen with an alkali and an enzyme such as pepsin, trypsin, chymotrypsin, papain and pronase, respectively, are preferably use. These collagens are preferred because a telopeptide site in the collagen molecule, having a high antigenicity, is removed by the treatment and therefore the antigenicity is lowered.

The source of the collagen is not particularly specified. Collagens derived from skin, bone, cartilage, tendon, organ and the like of mammalian animals such as cow, pig, rabbit sheep, mouse and the like, can be generally used. A collagen-like protein derived from fishes and birds can be also used.

When an alkali-solubilized collagen or an enzyme-solubilized collagen is used as the collagen membrane, a collagen solution layer is formed using a conventional method such as a coating method and a flowing into method, and then, the collagen membrane is formed by means of freeze-drying and the like. The thickness of the collagen solution layer is regulated so that the finally formed collagen membrane has a thickness of 2 mm to 20 mm, preferably 5 mm to 10 mm. If the thickness of the collagen membrane is less than 2 mm, the collagen is rapidly absorbed in a living body, resulting in insufficient effects. If the thickness is 20 mm or more, no notable problem will be caused, but a problem may be caused in the control of the operation. The collagen membrane is preferably formed into a porous membrane so that, when the membrane is implanted into a living body, cells can easily invade, elongate, and proliferate in the membrane. The concentration of the collagen solution, used here, which can be properly regulated depending on the thickness and the density of required collagen membrane, is 0.1 to 5% by weight, preferably 0.5 to 2% by weight. When the collagen membrane is formed into a porous membrane, a collagen solution bubbled by stirring is used.

The above freeze-drying procedure can be carried out according to a conventional method. In such a case, the collagen is desirably fiberized prior to the freeze-drying procedure to enhance the strength of the collagen membrane. The fiberizing procedure can be carried out by changing the hydrogen ion concentration of the collagen solution, or by elevating the temperature thereof.

Furthermore, a purified collagen derived from a living body can be used as it is, as the material of the collagen membrane. A purified human amnion or a purified human chorion obtained from a human placenta is preferred. Such a material contains human collagen as a main component. So that it has low antigenicity, procedures such as solubilization and coating can be omitted. The collagen should also have suitable strength.

The purified human amnion or the purified human chorion can be used as the collagen membrane in the manner as described in, for example, Japanese Laid-Open Patent Application (KOKAI) No. 56987/93. Namely, only a human fetal membrane is separated from a mass comprising human fetal membrane, placenta and umbilical cord, collected immediately after labor in a 1% benzalkonium-chloride solution or benzalkonium bromide solution, and an amnion or a chorion, which is the substrate type V collagen membrane, is peeled from the fetal membrane consisting of 4 layers. Then, remaining tissues and the like are physically or enzymatically removed, followed by washing with an ultrasonic wave to produce a purified human amnion or human chorion.

A human amnion has a structural difference between the two surfaces. One surface facing toward the fetus is smooth and comprises fine fibers having a thickness of $0.1\mu$ or less and cells hardly adhere to it. Another surface facing toward the chorion is rough and comprises thick fasciculus having a thickness of 0.5 to $0.2\mu$ is suitable for cell proliferation and take. Therefore, when the material for medical use of the present invention is used as an adhesion-preventing material, the mesh-like intermediary material is preferably interposed with two sheets of the collagen membrane of a purified human amnion so that the surfaces thereof facing toward the fetus are outside. On the other hand, if the material for medical use of the present invention is used for the purpose of cell proliferation or take, the mesh-like intermediary material is preferably interposed with two sheets of the collagen membrane of a purified human amnion so that the surfaces thereof facing toward the chorion are outside.

The above-described collagen membrane is subjected to a cross-linking treatment. The cross-linking treatment is carried out in order to fix the two sheets of collagen membrane closely adhered to each other in an integrated form, through an adhesive, described below, and also to regulate the decomposition/absorption rate of the collagen membrane, depending on the intended medical use of the material of the present invention. Namely, by properly changing the reaction conditions of the cross-linking treatment to produce a collagen membrane neither degradable nor absorbable in a living body, or a collagen membrane degradable and absorbable in a living body, and furthermore by combining the collagen membrane with a mesh-like intermediary material comprising a material neither degradable nor absorbable in a living body, or a material degradable and absorbable in a living body, described later, various materials applicable to an artificial organ and an artificial viscus, or applicable as a wound-covering material, a wound-prosthetic material, a wound-curing material, and the like, can be obtained.

For example, by combining a collagen membrane degradable and absorbable in a living body, with a mesh-like intermediary material comprising a material degradable and absorbable in a living body, the resulting material can be used as a suture-reinforcing material, a prosthetic material or an artificial organ as replaced with tissues of the living body in the process of regeneration. Also, by combining a collagen membrane degradable and absorbable in a living body with a mesh-like intermediary material comprising a material neither degradable nor absorbable in a living body, the resulting material can be used as a prosthetic material or an artificial organ which is required to permanently maintain the tissue strength of the living body after the collagen membrane is replaced by living tissues. By combining a collagen membrane non-degradable in a living body with a material neither degradable nor absorbable in a living body, the resulting material can be applied to an artificial organ such as an artificial valve which is required only to have a molding-processability and not to permanently react with living tissues at all.

A process for the cross-linking treatment may include glutaraldehyde cross-linking, an epoxy cross-linking or heat cross-linking. The glutaraldehyde cross-linking can be carried out by immersing the material in a glutaraldehyde solution having a concentration of 0.05 to 3%, preferably 0.1 to 2%, followed by air-drying. If the concentration is less than 0.05% the collagen membrane easily peels off. If the concentration is over 3% the collagen membrane is hardened, resulting in a loss of affinity for a living body. The glutaraldehyde cross-linking is presumed to proceed with a reaction of an amino group in the collagen molecule with an aldehyde group of glutaraldehyde.

The epoxy cross-linking can be carried out by immersing the material in a solution comprising an epoxy compound having 2 epoxy groups, a hardening-accelerator, and the like. For example, the material is immersed in 2% DENACOLE solution having a pH value of 10, prepared by adding 47.5 ml of 0.1M carbonate buffer and 47.5 ml of ethanol to 5 ml of original DENACOLE solution (manufactured by Nagase Industries), a hydrophilic cross-linking agent, for 12 to 24 hours at a room temperature, washed in water well, and air-dried. The epoxy cross-linking is presumed to proceed with a reaction of an amino group in the collagen molecule with an epoxy group in the epoxy compound.

The heat cross-linking can be carried out by heating the material in vacuo at 90° to 200° C. preferably 105° to 150° C., and dehydrating it to cause a cross-linking reaction.

The time for heating the material, which may be properly regulated depending on the heating temperature, the degree of reduced pressure, and the desired degree of cross-linking, is usually 6 to 24 hours. The heat cross-linking of collagen is presumed to proceed with the formation of a Schiff base or an aldol condensation between a sugar chain in the collagen molecule or an aldehyde group resulting from oxidization and lysine or hydroxylysine in the collagen molecule. In consideration of these points, as the collagen membrane comprising an alkali-solubilized collagen or an enzyme-solubilized collagen, a collagen originating from pig is preferred because it has a high sugar chain content and easily forms the cross-linking structure.

The mesh-like intermediary material imposed between the above collagen membranes may be preferably in the form of, for example, a mesh sheet, woven fabric, non-woven fabric, or porous sheet. The mean pore diameter is preferably 100 to 2000 μm from the viewpoint of the degradability or elasticity in a living body, or so that the collagen membranes can be closely adhered to each other through pores of the mesh-like intermediary material. If the mean diameter is less than 100 μm, the collagen membranes are less closely adhered to each other. If the mean pore diameter is over 2000 μm, cracks will form in the collagen membranes when sutured, resulting in a low transfixing property. The mean pore diameter is preferably 100 to 1500 μm, more preferably 150 to 1000 μm, most preferably 150 to 500 μm. The thickness is preferably 100 to 1000 μm. In the case of a non-woven fabric, the pore diameters differ from each other. Therefore, the mean pore diameter mentioned in the present invention is a mean value calculated by regarding the diameter of a circle having an area being the same as that of the pore as the pore diameter.

As the mesh-like intermediary material, a material degradable in a living body or a material non-degradable in a living body can be used. Namely, if it is intended to implant the material of the present invention into a living body, a material degradable in a living body can be used. If it is intended to permanently maintain the strength of regenerating tissues, or to apply the material to an artificial skin, a material non-degradable in a living body can be used.

As the material degradable in a living body, various kinds of material capable of being degraded through hydrolysis or enzymolysis, and absorbed in a living body can be used. The material should also have no toxicity and have some mechanical strength. A polyglycolic acid, a polylactic acid, a copolymer of glycolic acid and lactic acid, a polydioxanone, a copolymer of glycolic acid and trimethylene carbonate, a mixture of a polyglycolic acid and a polylactic acid, and the like can be preferably used.

As the material non-degradable in a living body, the usual synthetic high molecular compounds such as a silicone, a polytetrafluoroethylene, a polyethylene, a polypropylene, a polyethylene terephthalate, a polyurethane, a polyvinyl alcohol, and a nylon can be used.

The mesh-like intermediary material is preferably subjected to a hydrophilization treatment by plasma irradiation to improve the affinity for living tissues or the collagen membrane.

As the adhesive which adheres the above collagen membranes directly to each other, a gelatin solution or a collagen solution can be preferably used. As a raw material gelatin solution for the adhesive, purified gelatin listed in the Pharmacopoeia of Japan, can be generally used. As a collagen for a raw material of the collagen solution, an acid-solubilized collagen, an alkali-solubilized collagen and an enzyme-solubilized collagen can be used. The concentration of the gelatin solution is 1.0 to 5.0% by weight, preferably 2.0 to 3.0% by weight. The concentration of the collagen solution is 0.5 to 3.0% by weight, preferably 1.0 to 3.0% by weight.

The process for preparing the material for medical use of the present invention is explained below.

As the first step, the above mesh-like intermediary material is subjected to a plasma discharge treatment, then immersed in or coated with an adhesive comprising the above gelatin solution or the above collagen solution. Then, the mesh-like intermediary material is interposed between two sheets of the above collagen membrane to laminate them. If a purified human amnion is used as the collagen membrane, the mesh-like intermediary material is interposed so that the required surface of the amnion is outside, depending on the purpose.

As the second step, the thus obtained laminated material is kept under reduced pressure of 10 to 20 Torr at room temperature for about 0.1 hour to remove air between the two sheets of collagen membrane or between the mesh-like intermediary material and the collagen membrane to closely adhere the two sheets of the collagen membrane to each other, and the laminated material is simultaneously dried. The second step can also be carried out by air-drying only, without the procedures under reduced pressure.

As the third step, the laminated material which had been dried under reduced pressure, is subjected to glutaraldehyde cross-linking, epoxy cross-linking or heat cross-linking to fix the collagen membranes in an integrated form and simultaneously make the laminated material neither degradable nor absorbable in a living body, or degradable and absorbable in a living body, depending on the intended use.

When required, the obtained-laminated material can be immersed in a glycerin solution and the like to afford a flexibility to the collagen membranes.

Through the above described steps, the material of the present invention comprising two sheets of collagen membrane adhered to each other with an adhesive and having interposed therebetween a mesh-like intermediary material can be obtained, and is applicable to an artificial organ or an artificial viscus, and applicable as a wound covering material, a wound prosthetic material, a wound curing material and the like.

Furthermore, the material of the present invention can be applicable as an adhesion-preventing material by subjecting the material of the present invention (wherein the collagen membrane comprises a material degradable and absorbable in a living body) to a succinylation treatment, causing most of the amino groups remaining in the collagen molecule to react with succinic anhydride. This succinylation can be carried out according to a usual method. For example, the material of the present invention is immersed in a mixture comprising 250 ml of 0.02 M borate buffer having a pH value of 9.0 and 50 ml of a 5% succinic anhydride solution in acetone for 1 to 48 hours, preferably 12 to 24 hours, washed with water, and dried under reduced pressure.

In order to confirm that the collagen membrane is succinylated, the material which has been succinylated is immersed in, for example, a 0.33% ninhydrin aqueous solution for 3 to 5 minutes. The ninhydrin coloring reaction is based on a condensation product resulting from a reaction of an amino group in the collagen molecule with ninhydrin, and as the collagen membrane is more succinylated, the membrane becomes non-dyeable.

EXAMPLES

The present invention will be more specifically explained with references to the following Examples, Comparative examples and Test examples.

Examples 1 and 2, and Comparative Examples 1 Through 4

Two kinds of mesh-like intermediary material comprising a polyglycolic acid, DEXON MESH (manufactured by Nihon Lederle Co.), PGA MESH (manufactured by Gunze Co.), and TGP 1800 comprising a polyethylene terephthalate (manufactured by Gunze Co.) were obtained, and, on a sheet of aluminium foil having the same size as that of the above intermediary material, were hydrophilized by a discharge treatment for 10 minutes by using a Tesla coil. Then, it was immersed in a 2.0% gelatin solution or a 1.0% collagen solution. The mean pore diameter of the mesh-like intermediary material is 50 μm for DEXON MESH, 200 μm for PGA MESH, and 10 μm for TGP 1800. As the gelatin, purified gelatin listed in the Pharmacopoeia of Japan, and as the collagen, type I collagen obtained from pig were used.

An amnion was peeled from a human fetal membrane, and foreign matters were removed from the amnion. Then the amnion was subjected to a ficin treatment by immersing it in 0.01% ficin solution in 0.2 M phosphate buffer, having a pH value of 7.4, and was subjected to an ultrasonic treatment in purified water to completely remove foreign matters. The amnion was immersed in a benzalkonium chloride aqueous solution. Using 2 sheets of the thus obtained purified human amnion, the mesh-like intermediary material after being immersed in the collagen solution was interposed therebetween for lamination.

The obtained laminated material was dried by allowing it to stand in a desiccator which-employs phosphorus pentoxide as a drying agent at room temperature for 15 hours. After drying, the desiccator was connected to a vacuum pump, and aspirated for 10 minutes to cause the two sheets of the purified human amnion to closely adhere to each other.

Then, the thus obtained laminated material was placed in a thermostatic bath together with the desiccator, the temperature of the bath was set at 105° C. in vacuo, and the laminated material was allowed to stand for 24 hours after the temperature began to elevate to cause a cross-linking reaction. Furthermore, the laminated material was immersed in a 5% glycerin solution for 30 minutes to afford a flexibility to the purified human amnion, and dried in a desiccator under reduced pressure to give the material for medical use.

Examples 3 Through 6

A material for medical use was prepared by using PGA MESH having a mean pore diameter of 200 μm as used in Example 1, in the same manner as in Example 1 except that a cross-linking treatment was performed by immersing the laminated material in 0.05%, 0.1%, 0.5%, and 1.0% glutaraldehyde solutions for 1 hour in place of the heat cross-linking treatment.

Comparative Examples 5 and 6

As the mesh-like intermediary material, PGA MESH having a mean pore diameter of 200 μm, used in Example 1, was used, and both surfaces thereof were treated by using an apparatus for plasma irradiation for 5 minutes, respectively, for hydrophilization.

Fifty ml of a 1% solution of an enzyme-solubilized collagen originating from porcine skin, having a pH value of 3.0, or 50 ml of a 1% solution of an alkali-solubilized collagen originating from porcine skin, having a pH value of 9.0, was stirred with a stirrer at 3000 rpm for 5 minutes to bubble it. Both surfaces of PGA MESH were coated with the solution, and subjected to a neutralization treatment under an ammonia atmosphere for 30 minutes so as to gelatinize the collagen. After the neutralization treatment, the resulting material was well washed with distilled water to remove ammonia, and immediately freeze-dried to produce PGA MESH coated with porous collagen layer. After freeze-drying, the material was furthermore subjected to a heat treatment at 105° C. for 12 hours in vacuo to produce a material for medical use.

Example 7

The material for medical use prepared in Example 1 was immersed in a mixed solution comprising 250 ml of 0.02 M borate buffer having a pH value of 9.0 and 50 ml of 5% succinic anhydride solution in acetone at a room temperature for 24 hours, washed with water, and air-dried overnight for succinylization.

Comparative Example 7

A polyglycolic acid yarn of 12 filament and 35 denier, obtained by a fusion-preventing method was treated with heat at 106° C. for 3 hours, and knitted with an apparatus for tubularly knitting to produce a tubular plain fabric. The obtained fabric was 4-fold laminated and subjected to needle-punching so as to have a polyglycolic acid non-woven fabric wherein interstices can be substantially invisible. The fabric was subjected to a heat press at 100° C. for 5 minutes to remove the hairiness or frays. The polyglycolic acid non-woven fabric was cut into pieces 10 cm in size, and both surfaces thereof were treated with a plasma irradiation apparatus for 5 minutes for hydrophilization.

Fifty ml of a 1% solution of enzyme-solubilized collagen originating from porcine skin, having a pH value of 3.0 was stirred with a stirrer at 3000 rpm for 5 minutes to bubble it, applied to one surface of the above polyglycolic acid non-woven fabric, and subjected to a neutralization treatment for 30 minutes under an ammonia atmosphere to gelatinize the collagen. After the neutralization treatment, the resulting material was well washed in distilled water to remove ammonia, and immediately freeze-dried to produce the polyglycolic acid non-woven fabric coated with porous collagen layer. After freeze-drying it, it was treated with heat at 105° C. in vacuo for 12 hours to produce a material for medical use.

Test Example 1

The peeling strength of the material for medical use, prepared in Examples 1 through 7 and Comparative examples 1 through 7 was determined under dry conditions. For measurement of the peeling strength of the collagen membrane, the material for medical use was cut into pieces, 1 cm in size, to have produce samples for the test. One surface of the sample was adhered to a floor face, and another surface was adhered to a plastic plate equipped with a thread. The thread was connected with a strain gauge, and the thread was pulled until the collagen membrane peeled off to determine the strain of the thread.

Also, the material for medical use was immersed in a physiological saline at 37° C. to determine whether the collagen membrane peeled off. The results are shown in Table 1.

and 2 and Examples 4 through 6, a needle for operation could be easily passed through pores of the mesh-like intermediary materials, and the collagen membrane was not destroyed. But, in the case of Comparative examples 1 through 6, the collagen membrane was destroyed.

Also, a part of pericardium, 5 cm in size, of a dog, weighting 15 kg, was resected, and the resected part was replaced with the material for medical use prepared in Example 7.

When the operation was carried out again after 6 weeks, the pericardium regenerated without adhesion.

A part of an oviduct muscle, 2 cm in size, and a part of a peritoneum, 2 cm in size, of a rabbit weighing 3 kg, were resected, and the materials prepared in Examples 4 through 6 and Example 7 were inserted into the resected site. When the operation was carried out again after 3 weeks, the oviduct and the peritoneum did not show adhesion.

The material for medical use of the present invention has excellent affinity for a living body and tissue-compatibility, and possesses low antigenicity because a collagen membrane is employed. Since the mean pore diameter of the mesh-like intermediary material is as large as 100 to 2000

TABLE 1

| | Mesh-like intermediary material | Mean pore diameter (μm) | Collagen-like membrane | Adhesive | Cross-linking treatment | Peeling test of collagen-like membrane | |
|---|---|---|---|---|---|---|---|
| | | | | | | Peeling strength (g/cm²) | Peeling test in physiological saline at 37° C. |
| Comparative Example 1 | DEXON MESH | 50 | Purified human amnion | 2.0% Gelatin solution | Heat cross-linking | 0 | Peeling after 1 day |
| Comparative Example 2 | DEXON MESH | 50 | Purified human amnion | 1.0% Collagen solution | Heat cross-linking | 0 | Peeling after 1 day |
| Comparative Example 3 | TGP 1800 | 10 | Purified human amnion | 2.0% Gelatin solution | Heat cross-linking | 0 | Peeling after 1 day |
| Comparative Example 4 | TGP 1800 | 10 | Purified human amnion | 1.0% Collagen solution | Heat cross-linking | 0 | Peeling after 1 day |
| Example 1 | PGA mesh | 200 | Purified human amnion | 2.0% Gelatin solution | Heat cross-linking | 1033 | No peeling after 14 days |
| Example 2 | PGA mesh | 200 | Purified human amnion | 1.0% Collagen solution | Heat cross-linking | 1030 | No peeling after 14 days |
| Example 3 | PGA mesh | 200 | Purified human amnion | 2.0% Gelatin solution | 0.05% GA solution cross-linking | 337 | Peeling after 3 to 5 days |
| Example 4 | PGA mesh | 200 | Purified human amnion | 2.0% Gelatin solution | 0.1% GA solution cross-linking | 708 | No peeling after 14 days |
| Example 5 | PGA mesh | 200 | Purified human amnion | 2.0% Gelatin solution | 0.5% GA solution cross-linking | 722 | No peeling after 14 days |
| Example 6 | PGA mesh | 200 | Purified human amnion | 2.0% Gelatin solution | 1.0% GA solution cross-linking | 800 | No peeling after 14 days |
| Comparative Example 5 | PGA mesh | 200 | Alkali-solubilized collagen | Not used | Heat cross-linking | 20 | Peeling after 1 day |
| Comparative Example 6 | PGA mesh | 200 | Enzyme-solubilized collagen | Not used | Heat cross-linking | 20 | Peeling after 1 day |
| Example 7 | PGA mesh | 200 | Purified human amnion | 2.0% Gelatin solution | Heat cross-linking | 1000 | No peeling after 14 days |
| Comparative Example 7 | Polyglycolic acid non-woven fabric | Almost no mesh | Enzyme-solubilized collagen | Not used | Heat cross-linking | 0 | Peeling after 1 day |

Test Example 2

In order to confirm the usefulness of the material medical use of the present invention, the materials prepared in Examples 1 and 2, Examples 4 through 6 and Comparative examples 1 through 6, 1 cm in size, were sutured to a lung, heart, intestine and muscle of a rabbit, weighing 3 kg, and a dog, weighing 15 kg, using a polypropylene suture. As a result, in the case of the materials prepared in Examples 1

μm, a surgical needle can be easily passed through the pore when it is sutured to an organ or a trauma part. Since the mesh-like intermediary material is interposed between the collagen membranes, and the mechanical strength of the collagen membrane is enhanced by a cross-linking treatment, the collagen membrane is not easily destroyed when a surgical needle is passed through it. Thus, it has excellent in transfixing properties. Also, since two sheets of the collagen membrane, closely adhered to each other through an adhesive, are fixed in an integrated form by a cross-linking treatment, the collagen membrane does not peel off and another operation is not required for re-implantation, when the material is implanted into a living body.

Furthermore, the collagen membrane is made degradable and absorbable in a living body, or made neither degradable nor absorbable in a living body by subjecting the collagen membrane to a cross-linking treatment. Therefore, by combining the collagen membrane with the mesh-like intermediary material comprising a material degradable and absorbable in a living body or a material non-degradable in a living body, the material of the present invention can be used as various materials for medical use.

I claim:

1. A material for medical use comprising two sheets of membrane of a purified collagen derived from a living body adhered to each other with an adhesive and having interposed therebetween a mesh-like intermediary material, wherein the mean pore size of the mesh-like intermediary material, is between 100 and 2000 μm.

2. The material of claim 1, wherein the membrane of a purified collagen derived from a living body is a collagen solubilized with an alkali or a collagen solubilized with an enzyme.

3. The material of claim 1, wherein the membrane of a purified collagen derived from a living body is of a human amnion or a human chorion.

4. The material of claim 3, wherein the mesh-like intermediary material is interposed with two sheets of the collagen membrane of a human amnion so that the surfaces thereof facing toward a fetus are outside.

5. The material of claim 3, wherein the mesh-like intermediary material is interposed with two sheets of the collagen membrane of a human amnion so that the surfaces thereof facing toward a chorion are outside.

6. The material of claim 1, wherein the mean pore size of the mesh-like intermediary material is 100 to 1500 μm.

7. The material of claim 1, wherein the mesh-like intermediary material is degradable and absorbable in a living body.

8. The material of claim 1, wherein the mesh-like intermediary material is not degradable and not absorbable in a living body.

9. The material of claim 7, wherein the intermediary material is a poly(glycolic acid), a poly(lactic acid), a copolymer of glycolic acid and lactic acid, a polydioxanone, a copolymer of glycolic acid and trimethylene carbonate or a mixture of a poly(glycolic acid) and a poly(lactic acid).

10. The material of claim 8, wherein the intermediary material is neither degradable nor absorbable in a living body and is a silicone, a polytetrafluoroethylene, a polyethylene, a polypropylene, a polyethylene terephthalate, a polyurethane, a polyvinyl alcohol or a nylon.

11. The material of claim 1, wherein the adhesive is a collagen solution or a gelatin solution.

12. A process for preparing a material for medical use comprising:

(a) laminating with an adhesive two sheets of membrane of a purified collagen derived from a living body having a mesh-like intermediary material interposed therebetween;

(b) maintaining the resulting laminated material under a reduced pressure so that the two sheets of membrane are adhered to each other through the mesh-like intermediary; and (c) cross-linking the laminated material.

13. The process of claim 12, wherein the material is subjected further to succinylation treatment.

14. The process of claim 12, wherein the membrane of a purified collagen derived from a living body is a collagen solubilized with an alkali or a collagen solubilized with an enzyme.

15. The process of claim 12, wherein the membrane of a purified collagen derived from a living body is of a human amnion or a human chorion.

16. The process of claim 15, wherein the mesh-like intermediary material is interposed with two sheets of the collagen membrane of a human amnion so that the surfaces therof facing toward a fetus are outside.

17. The process of claim 15, wherein the mesh-like intermediary material is interposed with two sheets of the collagen membrane of a human amnion so that the surfaces thereof facing toward a chorion are outside.

18. The process of claim 12, wherein the mean pore size of the mesh-like intermediary material is 100 to 2000 μm.

19. The process of claim 12, wherein the mesh-like intermediary material is degradable and absorbable in a living body.

20. The process of claim 12, wherein the mesh-like intermediary material is not degradable and not absorbable in a living body.

21. The process of claim 19, wherein the intermediary material is a poly(glycolic acid), a poly(lactic acid), a copolymer of glycolic acid and lactic acid, a polydioxanone, a copolymer of glycolic acid and trimethylene carbonate or a mixture of a poly(glycolic acid) and a poly(lactic acid).

22. The process of claim 20, wherein the intermediary material is a silicone, a polytetrafluoroethylene, a polyethylene, a polypropylene, a polyethylene terephthalate, a polyurethane, a polyvinyl alcohol or a nylon.

23. The process of claim 12, wherein the adhesive is a collagen solution or a gelatin solution.

* * * * *